US011629108B2

(12) United States Patent
Simon et al.

(10) Patent No.: US 11,629,108 B2
(45) Date of Patent: Apr. 18, 2023

(54) METHOD FOR RECOVERING A STREAM OF C2+ HYDROCARBONS IN A RESIDUAL REFINERY GAS AND ASSOCIATED INSTALLATION

(71) Applicant: TECHNIP FRANCE, Courbevoie (FR)

(72) Inventors: Yvon Simon, Andresy (FR); Bruno Destour, Rueil Malmaison (FR); Marco Valente, Puteaux (FR)

(73) Assignee: TECHNIP ENERGIES FRANCE, Nanterre (FR)

( * ) Notice: Subject to any disclaimer, the term of this patent is extended or adjusted under 35 U.S.C. 154(b) by 337 days.

(21) Appl. No.: 16/614,799

(22) PCT Filed: May 17, 2018

(86) PCT No.: PCT/EP2018/062992
§ 371 (c)(1),
(2) Date: Nov. 18, 2019

(87) PCT Pub. No.: WO2018/211036
PCT Pub. Date: Nov. 22, 2018

(65) Prior Publication Data
US 2020/0199046 A1    Jun. 25, 2020

(30) Foreign Application Priority Data
May 18, 2017 (FR) ..................... 17 54426

(51) Int. Cl.
*C07C 7/00* (2006.01)
*B01D 53/18* (2006.01)
(Continued)

(52) U.S. Cl.
CPC ............. *C07C 7/005* (2013.01); *B01D 53/18* (2013.01); *C07C 7/04* (2013.01); *C07C 7/09* (2013.01);
(Continued)

(58) Field of Classification Search
CPC .. C07C 7/005; C07C 7/04; C07C 7/09; C07C 7/11; B01D 53/18; B01D 53/00;
(Continued)

(56) References Cited

U.S. PATENT DOCUMENTS 6,662,589 B1 * 12/2003 Roberts ................. F25J 3/0247
62/425
10,767,924 B2    9/2020 Laugier et al.
(Continued)

FOREIGN PATENT DOCUMENTS

CN    102906232 A    1/2013
CN    104246400 A    12/2014
(Continued)

OTHER PUBLICATIONS

Jun. 11, 2018 English Translation of International Search Report in connection with PCT/EP2018/062992.
(Continued)

*Primary Examiner* — Thuan D Dang
(74) *Attorney, Agent, or Firm* — Locke Lord LLP; Alan B. Clement; Alicia J. Carroll

(57) ABSTRACT

This method comprises passing a residual stream into a flash drum to form a gaseous overhead flow and liquid bottom flow, and feeding the bottom flow into a distillation column, It comprises cooling the overhead flow in a heat exchanger to form a cooled overhead flow.
It comprises the extraction of a gaseous overhead stream at the head of the distillation column, and the formation of at least one effluent stream from the overhead stream and/or from the top stream.
The separation of the cooled overhead flow comprises passing the cooled overhead flow into an absorber, and
(Continued)

injecting a methane-rich stream into the absorber to place the cooled overhead flow in contact with the methane-rich stream.

11 Claims, 1 Drawing Sheet

(51) Int. Cl.
| | |
|---|---|
| *C07C 7/04* | (2006.01) |
| *C07C 7/09* | (2006.01) |
| *C07C 7/11* | (2006.01) |
| *C10G 70/04* | (2006.01) |
| *C10G 70/06* | (2006.01) |
| *F25J 3/02* | (2006.01) |

(52) U.S. Cl.
CPC .............. *C07C 7/11* (2013.01); *C10G 70/041* (2013.01); *C10G 70/06* (2013.01); *F25J 3/0219* (2013.01); *F25J 3/0238* (2013.01); *F25J 2200/02* (2013.01); *F25J 2200/70* (2013.01); *F25J 2205/04* (2013.01); *F25J 2205/50* (2013.01); *F25J 2210/12* (2013.01)

(58) Field of Classification Search
CPC ........ C10G 70/041; C10G 70/06; C10G 7/00; C10G 5/06; F25J 3/0219; F25J 3/0238; F25J 2200/02; F25J 2200/70; F25J 2205/04; F25J 2205/50; F25J 2210/12; F25J 2205/30; F25J 2210/62; F25J 2230/30; F25J 3/0233; F25J 3/0252; F25J 3/00
See application file for complete search history.

(56) References Cited

U.S. PATENT DOCUMENTS

| | | |
|---|---|---|
| 2004/0148964 A1 | 8/2004 | Patel et al. |
| 2013/0102827 A1* | 4/2013 | Simon ................ C10G 70/043 422/119 |
| 2017/0191751 A1 | 7/2017 | Hudson et al. |
| 2019/0359484 A1* | 11/2019 | Van Willigenburg ... C10G 9/36 |

FOREIGN PATENT DOCUMENTS

| | | |
|---|---|---|
| EA | 000813 | 12/1999 |
| EA | 201201340 A1 | 4/2013 |
| EP | 3190098 A2 | 7/2017 |
| FR | 2957931 | 9/2011 |
| RU | 2144556 C1 | 1/2000 |
| WO | WO 2014/064172 | 5/2014 |

OTHER PUBLICATIONS

Jun. 11, 2018 English Translation of Written Opinion of International Searching Authority in connection with PCT/EP2018/062992.
Russian Search Report dated Jul. 19, 2021 issued in corresponding RU Application No. 2019136828.
Russian Office Action and English Translation thereof dated Jul. 20, 2021 issued in corresponding RU Application No. 2019136828.
Chinese Office Action and Search Report dated Dec. 16, 2021, issued for Chinese Patent Application No. 201880043307.6.

* cited by examiner

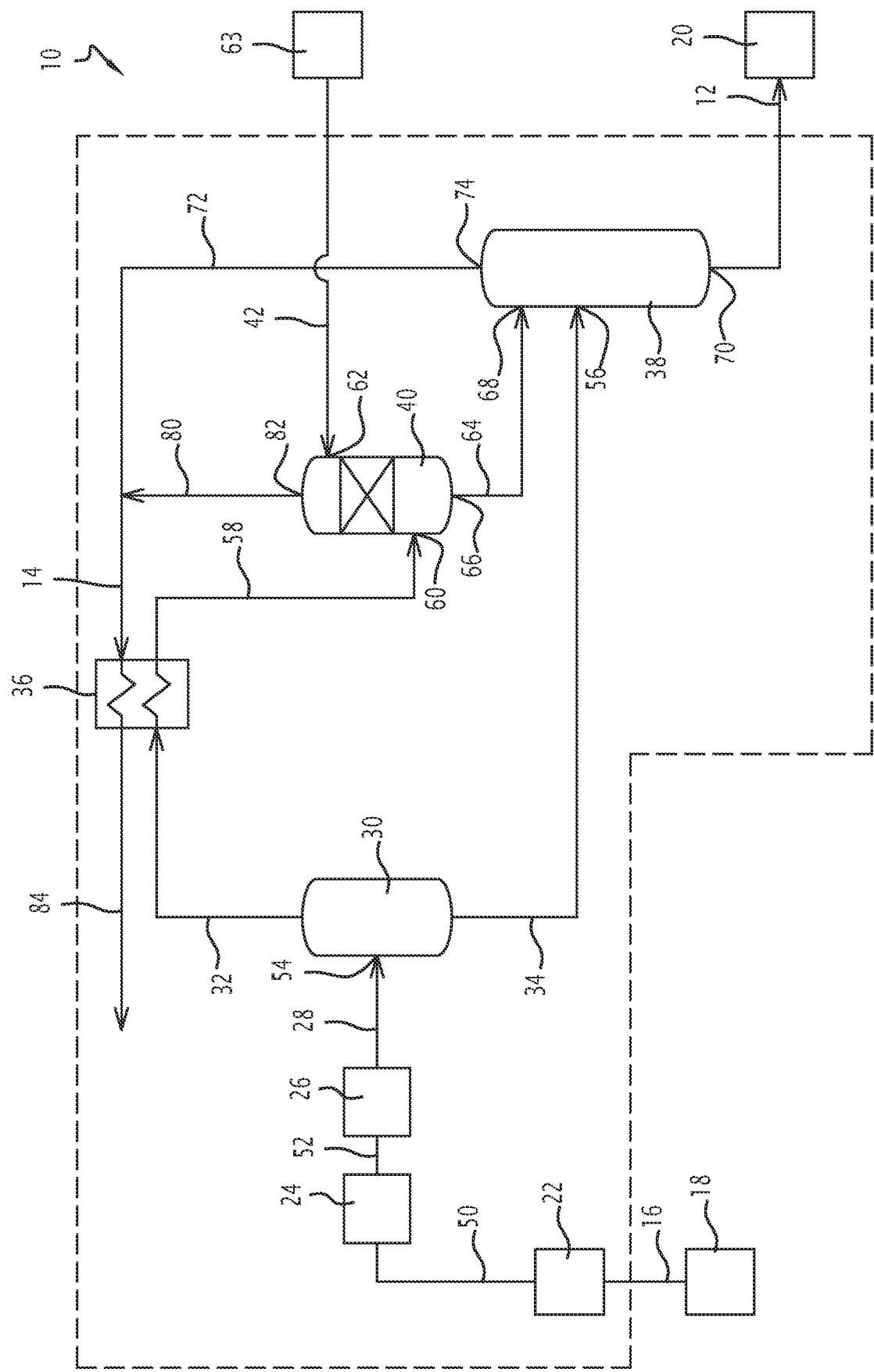

US 11,629,108 B2

METHOD FOR RECOVERING A STREAM OF C2+ HYDROCARBONS IN A RESIDUAL REFINERY GAS AND ASSOCIATED INSTALLATION

CROSS REFERENCE TO RELATED APPLICATIONS

This Application is a U.S. National Stage Entry of International Application no. PCT/EP2018/062992, filed on May 17, 2018 which claims priority to French Application no. FR1754426, filed on May 18, 2017, the entire contents of which are hereby incorporated herein by reference in their entirety.

The present invention relates to a method for recovering stream of C2+ hydrocarbons in a residual refinery gas, comprising the following steps:
- forming a residual stream from the residual refinery gas;
- feeding the residual stream into a flash drum to form a gaseous overhead flow and liquid bottom flow;
- feeding the bottom flow into a distillation column;
- cooling the overhead flow in a heat exchanger to form a cooled overhead flow;
- separating the cooled overhead flow into a liquid lower stream feeding the distillation column and into a gaseous top stream;
- feeding the lower stream into the distillation column above the bottom flow;
- recovering the stream of C2+ hydrocarbons at the bottom of the distillation column;
- extracting a gaseous overhead stream at the head of the distillation column;
- forming at least one effluent stream from the overhead stream and/or from the top stream;
- heating the or each effluent stream in the heat exchanger via heat exchange with the overhead flow.

Said method is intended to be implemented in a unit for recovering refinery off-gases for reuse of the content of these gases.

In manner known per se, refinery gases have a high light hydrocarbon content. In some cases, they are directly sent towards fuel gas networks then being reused as fuel. However, some light hydrocarbons have a significant market value. Ethylene, propylene, hydrogen in particular are products which can be sold directly. Ethane, propane, C4+ hydrocarbons can also be used to feed cracking furnaces.

The recovery of these hydrocarbons is therefore able to improve the productivity of a refinery or steam cracking unit receiving these residual gases, whether or not integrated in the refinery.

To recover these hydrocarbons, it is known from U.S. Pat. No. 3,320,754 for example to carry out successive cooling, condensation and separation steps in successive vessels to lower the temperature of the residual refinery gas stream.

The liquid collected in the last vessel is directed into a methane-removing column to allow separation between methane and light gases on one side and C2+ hydrocarbons on the other side.

The gases collected in the last vessel form an effluent stream that is heated in a cold box by cooling a fraction of the residual gas.

In an improvement on the method described in U.S. Pat. No. 3,320,754, to improve the recovery of C2+ hydrocarbons, the effluent stream leaving the cold box is then expanded in a dynamic expansion turbine.

The expanded stream is returned to the cold box to provide the negative kilocalories required for partial condensation of the residual gas flow upstream of the last vessel, from a temperature of substantially −100° C. down to a temperature of −110° C. to −115° C.

The cold supplied by the dynamic expansion turbine is therefore necessary to obtain a significant drop in the temperature of the gases to within the required range, which minimises losses of ethylene and ethane in the overhead gas of the distillation column.

However, the presence of a dynamic expansion turbine complicates implementation of the method and of the installation associated with this implementation.

The installation must therefore be equipped with the dynamic expansion turbine and with a cold box of complex structure to circulate the gas leaving the dynamic expansion turbine.

This requires a major initial investment and takes up significant space within the installation. In addition, the dynamic expansion turbine must undergo regular maintenance and may break down thereby limiting reliability and the productivity of the method.

It is one objective of the invention to provide a method with which it is possible efficiently and reliably to recover valuable products from residual refinery gases, whilst limiting investment and operating costs of the method.

For this purpose, the subject of the invention is a method in which separating the cooled overhead flow comprises feeding the cooled overhead flow into an absorber and injecting a methane-rich stream into the absorber to place the cooled overhead flow in contact with the methane-rich stream.

The method of the invention may comprise one or more of the following features taken alone or in any technically feasible combination:
- the methane-rich stream is a liquid stream;
- the methane molar content in the methane-rich stream is higher than 90 mole %;
- the methane-rich stream is formed from a thermal steam cracking unit without passing through the distillation column or through the flash drum;
- the temperature of the residual stream before entering the flash drum is lower than −80° C. and advantageously it is between −90° C. and −100° C.;
- the overhead flow circulates from the flash drum through the heat exchanger as far as the absorber without static or dynamic expansion in an expansion valve or dynamic expansion turbine;
- the heat exchanger is a two-flow heat exchanger, the method comprising the mixing of the overhead stream and/or top stream to form the effluent flow, the overhead flow being cooled exclusively by the stream of effluent between the flash drum and the absorber;
- the heat exchanger is a three-flow heat exchanger, the method comprising the formation of a first effluent stream from the overhead stream and a second effluent stream from the top stream, the overhead flow being cooled exclusively by the first effluent stream and by the second effluent stream between the flash drum and the absorber;
- the difference in temperature between the cooled overhead flow and overhead flow is greater than 2° C. in absolute value;
- the stream of C2+ hydrocarbons contains more than 90 mole % of the C2+ hydrocarbons contained in the residual stream;
- the method comprises a prior purification step and/or successive steps of cooling and separation of the residual refinery gas;

the methane-rich stream is advantageously expanded in a static expansion valve before being injected into the absorber;

the methane-rich stream is at least partly vaporized in the dynamic expansion valve;

the or each effluent stream is formed from the overhead stream and/or top stream without passing through a static expansion valve and/or a dynamic expansion turbine;

no fraction of the gaseous overhead stream enters the absorber;

the gaseous overhead stream is mixed with the top gaseous stream downstream of the absorber, without passing through the absorber;

the entirety of the overhead gaseous flow derived from the flash drum enters into the heat exchanger;

the entirety of the cooled overhead flow derived from the heat exchanger enters into the absorber.

A further subject of the invention is a installation for recovering a stream of C2+ hydrocarbons from a residual refinery gas, comprising:

a flash drum intended to form a gaseous overhead flow and liquid bottom flow, the flash drum comprising an inlet to receive a residual stream formed from the residual refinery gas;

a distillation column having an inlet for entry the bottom flow;

a heat exchanger intended to cool and condense the overhead flow at least in part;

a separator dividing the cooled overhead flow into a liquid lower stream feeding the distillation column and into a gaseous top stream;

an inlet for feeding the lower stream into the distillation column and positioned above the inlet for feeding the bottom flow;

an outlet to recover the stream of C2+ hydrocarbons at the bottom of the distillation column;

an outlet to extract a gaseous overhead stream at the head of the distillation column;

an assembly to form at least one effluent stream from the overhead stream and/or top stream;

an inlet for feeding the or each effluent stream into the heat exchanger, the effluent stream intended to be heated in the heat exchanger via heat exchange with the overhead flow;

characterized in that the separator of the cooled overhead flow comprises an absorber provided with an inlet for feeding the cooled overhead flow, and with an inlet for injection of a methane-rich stream to place the cooled overhead flow in contact with the methane-rich stream.

The installation of the invention may comprise one or more of the following features taken alone or in any technically feasible combination:

the inlet for injection of the methane-rich stream is connected to a thermal steam cracking unit without passing through the distillation column or through the heat exchanger;

the heat exchanger is a two-flow heat exchanger, the installation comprising a mixer intended to mix the overhead stream with the top stream, the overhead flow able to be cooled exclusively by the effluent stream between the flash drum and the absorber;

the heat exchanger is a three-flow heat exchanger, the installation comprising an assembly to form a first effluent stream from the overhead stream and a second effluent stream from the top stream, the overhead flow being cooled exclusively by the first effluent stream and by the second effluent stream between the flash drum and the absorber;

the installation comprises an upstream purification unit and/or upstream stages for cooling and separation of the residual refinery gas, connected to the inlet for feeding the residual stream into the flash drum.

The invention will be better understood on reading the following description given solely as an example and with reference to the appended drawings in which:

FIG. 1 is a summary schematic illustrating a first installation intended to implement a method of the invention.

A first installation 10 intended to recover a stream 12 of C2+ hydrocarbons and an effluent stream 14 from a crude residual refinery gas 16 using a method of the invention is schematically illustrated in FIG. 1.

The installation 10 is connected upstream to a refinery 18 producing the crude residual gas 16. The installation 10 is connected downstream to an ethylene fractionating and/or recovery plant 20.

The installation 10 comprises a purification unit 22 intended to remove contaminants contained in the residual refinery gas 16, a compression unit 24 and advantageously one or more cooling and separation stages 26 intended to produce a residual stream 28.

The installation 10 also comprises a flash drum 30 intended to receive the residual stream 28 to produce a gaseous overhead flow 32 and a liquid bottom flow 34, a two-flow heat exchanger 36 intended to cool the gaseous overhead flow 32, and a distillation column 38.

In the invention, the installation 10 also comprises an absorber 40 positioned between the heat exchanger 36 and the distillation column 38, the absorber 40 being fed with a methane-rich stream 42.

The purification unit 22 comprises at least one stage for removal of heavy metals and acid gases, and optionally a unit for removal of oxygen, a unit for water removal and a unit for intensive impurity removal.

The compression unit 24 comprises at least one compressor, it can be located upstream or downstream of the purification unit 22.

Each cooling and separation stage 26 comprises at least one heat exchanger intended to obtain gradual decrease in temperature of the residual gas to create a liquid fraction and a gaseous fraction, at least one flash drum intended to separate the liquid fraction and gaseous fraction after cooling, and optionally a fractionating column having the role of limiting the content of hydrocarbons in the stream 28 that are heavier than ethane.

In the remainder hereof the percentages are molar percentages by default. Pressures are expressed in barg.

The streams described in the installation also refer to the pipes in which they are conveyed.

A description will now be given of the implementation of the first method of the invention.

Initially, at least one crude gas 16 derived from the refinery 18 is recovered. For example, the crude gas 16 comprises between 1 mole % and 20 mole % of nitrogen, between 5 mole % and 60 mole % of hydrogen, between 10 mole % and 70 mole % of methane, between 5 mole % and 50 mole % of C2 hydrocarbons, between 0 mole % and 5 mole % of C3 hydrocarbons and between 0 mole % and 4 mole % of C4+ hydrocarbons.

The crude gas 16 generally comprises contaminants such as oxygen, nitrogen oxides, arsenic, ammonia, mercury, carbon monoxide, carbon dioxide. The crude gas generally comprises between 1 and 10 mole % of the above-listed contaminants.

The crude gas 16 is directed into the purification unit 22 to produce a purified gas 50 having an impurity content lower than that of the crude gas and in particular that is globally lower than 1 mole %.

The purified crude gas 50 is next compressed in the compression unit 24 to a pressure higher than 10 barg, and in particular of between 10 barg and 30 barg.

The compressed purified gas 52 leaving the compression unit 24 enters each successive cooling and separation stage for partial condensation and to produce the residual stream 28.

The residual stream 28 generally comprises between 1 mole % and 25 mole % of nitrogen, between 5 mole % and 70 mole % of hydrogen, between 10 mole % and 80 mole % of methane, between 5 mole % and 45 mole % of C2 hydrocarbons, between 0 mole % and 1 mole % of C3 hydrocarbons, and less than 1 mole % of C4+ hydrocarbons.

It has a temperature lower than −80° C. and advantageously it is between −90° C. and −100° C. It has a pressure higher than 10 barg and advantageously it is between 10 barg and 30 barg.

The residual stream 28 is sent into the flash drum 30 through an inlet 54 and is separated therein into the gaseous overhead flow 32 and liquid bottom flow 34.

The liquid bottom flow 34 is expanded advantageously in a static expansion valve and directed into the distillation column 38 through a first inlet 56.

The pressure of the liquid bottom flow 34, at the inlet 56, is less than 15 barg and advantageously between 8 barg and 12 barg.

The gaseous overhead flow 32 is directed into the heat exchanger 36 and on leaving the heat exchanger 36 produces a cooled overhead flow 58.

The cooled overhead flow 58 has a temperature of less than −90° C. and advantageously of between −100° C. and −130° C.

The cooled overhead flow 58 is advantageously at least partly condensed. It has a molar content of liquid higher than 5 mole % and in particular of between 5 mole % and 20 mole %.

The cooled overhead flow 58 then enters the absorber 40 through a lower inlet 60 positioned below the upper inlet 62 into which the methane-rich stream 42 is injected.

The overhead flow 32 circulates from the flash drum 30 through the heat exchanger 36 as far as the absorber 40 without static or dynamic expansion in an expansion valve or dynamic expansion turbine.

The absorber 40 is a column comprising trays and/or packing. It is able to place the overhead flow 58 in contact with the methane-rich stream 42 without chemical reaction.

The methane-rich stream 42 injected via the upper inlet 62 advantageously has a methane content higher than 95 mole %. It has a temperature of less than −90° C. and in particular of between −95° C. and −130° C.

The molar flow rate of the methane-rich stream 42 is low. Advantageously, the molar flow rate of the methane-rich stream 42 passing through the absorber is less than 25% of the molar flow rate of the overhead flow 32 at the outlet of the flash drum 30.

The methane-rich stream 42 is a liquid stream. It has a liquid content higher than 70 mole % before expansion through a static expansion valve to form the flow injected into the upper inlet 62.

The methane-rich stream 42 is produced for example in a cracking unit 63, in particular a steam cracking unit. The cracking unit 63 is located in the vicinity of the installation 10 e.g. in the refinery 18.

The methane-rich stream 42 is supplied to the absorber 40 directly from the cracking unit 63 without any passing through another item of equipment of the installation 10 such as the heat exchanger 36 changing the subject of the present invention.

A liquid lower stream 64 is produced at a lower outlet 66 of the absorber. The liquid lower stream 64 contains more than 85 mole % of the C2+ hydrocarbons contained in the overhead flow 58.

The lower stream 64 is expanded to a pressure lower than 15 barg and advantageously of between 8 barg and 12 barg.

It is afterwards passed under reflux into the distillation column 38 via an upper inlet 68 positioned above the inlet 56 for feeding the bottom flow 34.

The distillation column 38 operates at a pressure lower than 15 barg and advantageously of between 8 barg and 12 barg.

The stream 12 of C2+ hydrocarbons is produced at a recovery outlet 70 positioned at the bottom of the distillation column 38.

It contains between 70 mole % and 99 mole % of the C2+ hydrocarbons contained in the residual stream 28. The stream 12 of C2+ hydrocarbons is then directed to an ethylene fractionating and/or recovery plant 20.

A gaseous overhead stream 72 is recovered at an extraction outlet 74 positioned at the head of the distillation column 38. This stream 72 contains more than 95 mole % of the methane injected into the column 38.

The gaseous overhead stream 72 has a temperature lower than −95° C. and in particular of between −100° C. and −130° C.

Simultaneously, a gaseous top stream 80 is produced at an upper outlet 82 positioned at the head of the absorber 40.

The top stream 80 is extensively cooled. It has a temperature lower than the temperature of the gaseous overhead stream 72 and of the overhead flow 32. The temperature of the top stream is lower than −100° C. and in particular it is between −110° C. and −130° C.

The top stream 80 is expanded to a pressure lower than 8 barg and of between et 2 barg and 6 barg, and is then mixed in a mixer-forming branch pipe with the overhead stream 72 to produce the effluent stream 14.

The temperature of the effluent stream 14 is lower than −95° C. and in particular it is between −100° C. and −130° C.

It is passed into the heat exchanger 36 for heat exchange with the overhead flow 32 and to cool the overhead flow 32. The difference in temperature between the cooled overhead flow 58 and overhead flow 32 either side of the heat exchanger 36 is greater than 5° C. in absolute value.

The heated effluent stream 84 recovered on leaving the heat exchanger 36 is sent to a hydrogen fractionating unit and/or towards a fuel gas network.

In one operational example of embodiment of the invention, the operating conditions are the following:

| Stream | Temperature (° C.) | Pression (barg) |
| --- | --- | --- |
| 12 | −36 | 10.1 |
| 32 | −96 | 16.7 |
| 58 | −110 | 16.5 |
| 64 | −111 | 16.5 |

-continued

| Stream | Temperature (° C.) | Pression (barg) |
|---|---|---|
| 72 | −101 | 9.8 |
| 80 | −120 | 16.4 |

In the method of the invention, the thermal power needed to cool the gaseous overhead flow 32 is exclusively supplied by the effluent stream 14 derived from the absorber 40 and distillation column 38, without static or dynamic expansion of this stream 14 in an expansion valve or dynamic expansion turbine.

It is therefore not necessary to provide a dynamic expansion installation for the effluent stream 14 at the outlet of the heat exchanger 36, or upstream thereof, to supply the negative kilocalories required for cooling of the overhead flow 32.

The feeding of the methane-rich stream 42 into the absorber 40 is sufficient to produce a cooled gaseous top stream 80 depleted of C2+ and having the thermal power needed for cooling. The heat exchanger 36 is therefore of very simple structure since it is limited to two flows.

The investment layout to build the installation 10 required to implement the method is substantially reduced, since this installation 10 does not require a dynamic expansion turbine to produce the cold needed for cooling the overhead flow 32 to the desired temperatures. The installation 10 is also more compact.

The maintenance of the installation 10 is largely simplified due to the absence of a key rotating element and to increased reliability.

This is achieved without detriment to the recovery of C2+ hydrocarbons, not only under continuous operation but also during transitory shutdowns of the installation 10.

In one variant (not illustrated), the heat exchanger 36 is a three-flow heat exchanger 36. A first effluent stream is composed of the overhead stream 72 and a second effluent stream is composed of the top stream 80 which are passed into the heat exchanger 36 separately to enter into heat exchange with the overhead flow 32. The overhead flow 32 is exclusively cooled by the first effluent stream and by the second effluent stream, between the flash drum 30 and the absorber 40.

The invention claimed is:

1. Method for recovering a C2+ hydrocarbons stream in a residual refinery gas, comprising:
    forming a residual stream from the residual refinery gas;
    feeding the residual stream into a flash drum to form a gaseous overhead flow and a liquid bottom flow;
    feeding the liquid bottom flow into a distillation column via an inlet;
    cooling the gaseous overhead flow in a heat exchanger to form a cooled overhead flow;
    separating the cooled overhead flow into a liquid lower stream and into a gaseous top stream;
    feeding the liquid lower stream into the distillation column via an upper inlet positioned above the inlet for feeding the liquid bottom flow;
    recovering the C2+ hydrocarbons stream at a bottom of the distillation column;
    extracting a gaseous overhead stream at a head of the distillation column;
    forming at least one effluent stream from the gaseous overhead stream and/or from the gaseous top stream;
    heating the at least one effluent stream in a heat exchanger via heat exchange with the gaseous overhead flow;
    wherein separating the cooled overhead flow comprises feeding the cooled overhead flow into an absorber, and injecting a methane-rich stream into the absorber to place the cooled overhead flow in contact with the methane-rich stream, wherein the molar content of methane in the methane-rich stream is higher than 90 mole %.

2. The method according to claim 1, wherein the methane-rich stream is a liquid stream.

3. The method according to claim 1, wherein the methane-rich stream is formed from a thermal steam cracker, without passing through the distillation column or through the flash drum.

4. The method according to claim 1, wherein the temperature of the residual stream before entering the flash drum is lower than −80° C.

5. The method according to claim 4, wherein the temperature of the residual stream before entering the flash drum is between −90° C. and −100° C.

6. The method according to claim 1, wherein the overhead flow circulates from the flash drum through the heat exchanger as far as the absorber without static or dynamic expansion in an expansion valve or dynamic expansion turbine.

7. The method according to claim 1, wherein the heat exchanger is a two-flow heat exchanger, the method comprising mixing the overhead stream and the top stream to form the effluent stream, the overhead flow being cooled exclusively by the effluent stream between the flash drum and the absorber.

8. The method according to claim 1, wherein the heat exchanger is a three-flow heat exchanger, the method comprising forming a first effluent stream from the overhead stream and a second effluent stream from the top stream, the overhead flow being cooled exclusively by the first effluent stream and by the second effluent stream between the flash drum and the absorber.

9. The method according to claim 1, wherein a temperature difference between the cooled overhead flow and the overhead flow is greater than 2° C. in absolute value.

10. The method according to claim 1, wherein the C2+ hydrocarbons stream contains more than 90 mole % of the C2 hydrocarbons contained in the residual stream.

11. The method according to claim 1 comprising a prior purification and/or successive cooling and separating of the residual refinery gas.

* * * * *